US010424403B2

(12) United States Patent
Fung et al.

(10) Patent No.: US 10,424,403 B2
(45) Date of Patent: Sep. 24, 2019

(54) ADAPTIVE MEDICAL DOCUMENTATION SYSTEM

(71) Applicant: Siemens Aktiengesellschaft, Munich (DE)

(72) Inventors: Glenn Fung, Madison, WI (US); Joseph Marcus Overhage, Zionville, IN (US); Jan DeHaan, Hawley, PA (US); Faisal Farooq, Norristown, PA (US); Balaji Krishnapuram, King of Prussia, PA (US); John D Haley, Chester Springs, PA (US); Sebastian Philipp Brandt, Manchester (GB); Luigi Iannone, London (GB); Nicholas Drummond, Heaton Mersey (GB); Ignazio Palmisano, Manchester (GB)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/166,102

(22) Filed: Jan. 28, 2014

(65) Prior Publication Data

US 2014/0214451 A1 Jul. 31, 2014

Related U.S. Application Data

(63) Continuation-in-part of application No. 14/039,125, filed on Sep. 27, 2013.

(60) Provisional application No. 61/757,305, filed on Jan. 28, 2013.

(51) Int. Cl.
*G16H 10/60* (2018.01)
*G06F 19/00* (2018.01)
*G16H 50/30* (2018.01)

(52) U.S. Cl.
CPC ............ *G16H 10/60* (2018.01); *G06F 19/00* (2013.01); *G06F 19/324* (2013.01); *G16H 50/30* (2018.01)

(58) Field of Classification Search
CPC ........ G06Q 10/00; G06Q 50/22; G06Q 50/24; G16H 10/60; G16H 50/30; G06F 19/00; G06F 19/324
USPC ....................................................... 705/2, 3
See application file for complete search history.

(56) References Cited

U.S. PATENT DOCUMENTS

| | | | |
|---|---|---|---|
| 4,733,354 A | 3/1988 | Potter et al. | |
| 5,222,236 A | 6/1993 | Potash et al. | |
| 5,522,066 A * | 5/1996 | Lu | G06F 16/258 707/769 |
| 5,619,708 A | 4/1997 | Ho | |

(Continued)

FOREIGN PATENT DOCUMENTS

WO 2001069444 9/2001

OTHER PUBLICATIONS

Health Data Management, "Is the Future in the Palm of Your Hand?", Jan. 2002, www.healthdatamanagement.com.

(Continued)

*Primary Examiner* — Joy Chng

(57) ABSTRACT

Adaptive medical data collection for medical entities may involve managing content by receiving data indicating a context, identifying at least one application or knowledge base associated with the context, designating the identified application or knowledge base as active, and accessing the active application or knowledge base to provide information at an interface point for a medical professionals and a patient.

23 Claims, 6 Drawing Sheets

(56) References Cited

U.S. PATENT DOCUMENTS

| | | | |
|---|---|---|---|
| 5,704,029 | A | 12/1997 | Wright, Jr. |
| 5,737,539 | A | 4/1998 | Edelson et al. |
| 5,764,992 | A | 6/1998 | Kullick et al. |
| 5,832,494 | A | 11/1998 | Egger et al. |
| 5,857,967 | A | 1/1999 | Frid et al. |
| 5,859,972 | A * | 1/1999 | Subramaniam ....... G06F 16/258 709/203 |
| 6,065,026 | A | 5/2000 | Cornelia et al. |
| 6,084,585 | A | 7/2000 | Kraft et al. |
| 6,119,130 | A * | 9/2000 | Nguyen ................ G06F 16/258 707/695 |
| 6,119,137 | A | 9/2000 | Smith et al. |
| 6,128,661 | A | 10/2000 | Flanagin et al. |
| 6,151,643 | A | 11/2000 | Cheng et al. |
| 6,195,667 | B1 | 2/2001 | Duga et al. |
| 6,199,115 | B1 | 3/2001 | DiRienzo |
| 6,209,004 | B1 | 3/2001 | Taylor |
| 6,345,278 | B1 | 2/2002 | Hitchcock et al. |
| 6,473,892 | B1 | 10/2002 | Porter |
| 6,476,828 | B1 | 11/2002 | Burkett et al. |
| 6,498,657 | B1 | 12/2002 | Kuntz et al. |
| 6,606,604 | B1 | 8/2003 | Dutta |
| 6,816,630 | B1 | 11/2004 | Werth et al. |
| 6,850,944 | B1 * | 2/2005 | MacCall ................ G06F 16/954 |
| 8,065,655 | B1 | 11/2011 | Deo et al. |
| 8,150,711 | B2 | 4/2012 | Kelly et al. |
| 2002/0055945 | A1 | 5/2002 | Endress et al. |
| 2002/0169764 | A1 * | 11/2002 | Kincaid ................ G06F 16/358 |
| 2002/0194028 | A1 | 12/2002 | Johnston et al. |
| 2003/0030656 | A1 | 2/2003 | Ang et al. |
| 2003/0037069 | A1 | 2/2003 | Davison |
| 2003/0074222 | A1 * | 4/2003 | Rosow .................. G06Q 10/02 705/2 |
| 2003/0076342 | A1 | 4/2003 | Cole et al. |
| 2003/0088438 | A1 * | 5/2003 | Maughan .............. G06Q 50/22 705/2 |
| 2003/0088565 | A1 | 5/2003 | Walter et al. |
| 2003/0101238 | A1 | 5/2003 | Davison |
| 2003/0120514 | A1 | 6/2003 | Rao et al. |
| 2003/0120635 | A1 * | 6/2003 | Bousfield ............ G06F 9/44594 |
| 2003/0224823 | A1 * | 12/2003 | Hurst ...................... G06F 21/10 455/558 |
| 2003/0233257 | A1 * | 12/2003 | Matian .................. G06Q 50/24 705/3 |
| 2004/0117348 | A1 * | 6/2004 | Miyakawa ............. G16B 45/00 |
| 2004/0153965 | A1 | 8/2004 | O'Rourke |
| 2006/0178908 | A1 * | 8/2006 | Rappaport ........... G06F 19/325 705/2 |
| 2006/0271556 | A1 | 11/2006 | Mukherjee et al. |
| 2007/0005154 | A1 | 1/2007 | Lancaster et al. |
| 2007/0130206 | A1 * | 6/2007 | Zhou ..................... G16H 10/60 |
| 2007/0178501 | A1 | 8/2007 | Rabinowitz et al. |
| 2007/0239043 | A1 | 10/2007 | Patel et al. |
| 2008/0059391 | A1 | 3/2008 | Rosales et al. |
| 2008/0081955 | A1 | 4/2008 | Eisenhandler et al. |
| 2008/0201280 | A1 | 8/2008 | Martin et al. |
| 2008/0208624 | A1 | 8/2008 | Morita et al. |
| 2008/0269571 | A1 | 10/2008 | Brown et al. |
| 2009/0024615 | A1 | 1/2009 | Pedro et al. |
| 2009/0083231 | A1 | 3/2009 | Eberholst et al. |
| 2009/0204439 | A1 | 8/2009 | Turton |
| 2010/0131883 | A1 * | 5/2010 | Linthicum .............. G06F 19/00 715/771 |
| 2010/0235330 | A1 * | 9/2010 | Reiner .................. G06F 16/284 707/690 |
| 2011/0179389 | A1 | 7/2011 | Douen |
| 2011/0184954 | A1 * | 7/2011 | Nelson .................... G06F 16/31 707/740 |
| 2011/0202486 | A1 | 8/2011 | Fung et al. |
| 2011/0257988 | A1 | 10/2011 | Denkamp et al. |
| 2012/0078062 | A1 | 3/2012 | Bagchi et al. |
| 2013/0304487 | A1 * | 11/2013 | Kuwayama ........... G16H 10/60 705/2 |
| 2014/0156670 | A1 | 6/2014 | Hosomi |

OTHER PUBLICATIONS

Courter, et al., "Mastering Microsoft Office 2000 Professional Edition", 1999, Sybex, Inc., pp. 225-237.

Muench, S., "Building Oracle XML Applications", O'Reilly & Associates, 2000, cover, copyright page and pp. 284-309, 375-387, and 433-499.

Marchal, B. "Applied XML Solutions, The Authoritative Solutions", Sam's 2000, cover, copyright page, and pp. 71-194, 208-214 and 329-499.

Final Office Action dated Jan. 29, 2016 in U.S. Appl. No. 14/039,125, 11 pages.

* cited by examiner

ADAPTIVE MEDICAL DOCUMENTATION SYSTEM

RELATED APPLICATIONS

The present patent document claims the benefit of the filing date under 35 U.S.C. § 119(e) of Provisional U.S. patent application Ser. No. 61/757,305, filed Jan. 28, 2013, and is a continuation-in-part under 37 C.F.R. § 1.53(b) of U.S. patent application Ser. No. 14/039,125 filed Sep. 27, 2013, both of which are hereby incorporated by reference.

FIELD OF THE INVENTION

The present embodiments relate to medical documentation customization. Specifically, the present embodiments relate to automatic medical documentation adaptation for predicted or probable patient medical conditions.

BACKGROUND

Medical entities acquire and store significant amounts of patient medical information for diagnosis and tracking purposes. Historically, this information was acquired using paper forms, filled out by patients or medical entity personnel. Also, medical entity personnel would need to know specifically which forms to provide to patients depending on the specific medical history, current condition of the patient, and any other information that may be relevant to medical care of the patient. Often, the multitude of forms actually used for a given patient would request the same information multiple times. These forms may then be stored in a paper file, for future references by medical entity personnel.

Electronic Medical Records (EMR) have become a standard storage technique for medical and health records for patients of medical practitioners and medical entities. EMRs contain a considerable amount of medical data for specific patients, from various sources and in various formats. Collections of EMRs for medical facilities provide medical records and history for most, if not all, patients in a medical entity.

The entry of data into an EMR, however, may still be a very complex issue involving the manual selection of proper electronic forms for particular patients. Medical facilities and medical entities face challenges in improving the quality of care for patients, as well as reducing costs and increasing revenue. Efficient and effective entry of information into medical systems and EMRs may aid in the pursuit of these goals by increasing availability of data relevant to the care of patients.

BRIEF SUMMARY

By way of introduction, the preferred embodiments described below include methods, computer readable media, and systems for adaptively requesting, organizing, and presenting medical information. Context of an interaction between a medical professional and a patient may be used to specifically tailor the information sources and applications a system uses to provide and receive medical information of the patient.

In a first aspect, a system may be provided for generating a document using at least one knowledge base. The system may involve a repository of data comprising a plurality of knowledge bases. The system may also involve an interface for receiving data comprising situational elements indicating a context from an application remote to the repository of data. The system may also involve a knowledge processor configured to determine at least one knowledge base associated with the indicated context, designate as active the at least one knowledge base associated with the indicated context, designate as inactive at least one knowledge base not associated with the indicated context, and provide data from at least one active knowledge base to the remote application, the provided data operational to generate a document based on at least the provided data.

In a second aspect, a method may be provided for generating a document at a workstation. The method may involve receiving data comprising situational elements, identifying at least one application from a plurality of applications, and at least one knowledge base from a plurality of knowledge bases associated with the received situational elements, designating the identified at least one knowledge base as active, and accessing at least one knowledge base designated as active to provide information to the workstation for generating a document based on the situational elements.

In a third aspect, a system may be provided for generating a document. The system may involve at least one memory operable to store a plurality of knowledge bases. The system may also involve at least one processor configured to cause the system to receive data comprising at least one situational element, identify at least one knowledge base from the plurality of knowledge bases using the at least one situational element, designate the identified at least one knowledge base as active such that the active knowledge base may be accessed to provide data for a document, and designate at least one knowledge base as inactive that has not been identified using the at least one situational element.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
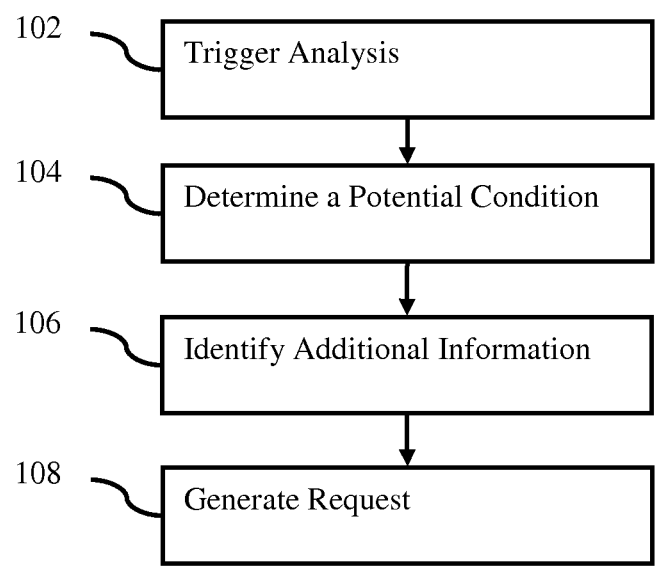
FIG. 1 is a flow chart diagram of one embodiment of a method for adaptive medical data collection.

The collection of medical data for a patient may adapt to information input into an electronic medical record (EMR) of a patient. The collection adapts based on inferences and conclusions that can be made using existing knowledge of the patient and other clinical information sources. Information currently being input may be combined with prior patient information and the other clinical information sources to suggest information related to a patient pertinent to current patient medical conditions. For example, previous patients having data similar to a current patient may be associated based on a distance metric relating to data of the current and previous patients. Data pertaining to associated previous patients may provide inferences and conclusions related to the current patient. The inferences and conclusions indicate suggested information specific to the current patient. A request for input of the suggested information specific to the patient may be made. The suggested information may further aid in the diagnosis or treatment of the patient. The suggested information may also be information related to a specific diagnosis or treatment determined to be relevant to a patient.

Adaptive medical information intake may take the form of a clinical documentation system. The clinical documentation system may be able to merge predefined form sections or templates such that information requests and presentation is not duplicated. Information being provided in real-time by a user and patient information extracted or accessed from previous patient EMRs may be used to determine which templates, or what parts of templates, are to be presented. The end result may be a real-time adaptable form constructed of templates, or template sections, specifically selected to suit a particular patient such that the constructed form contains all the relevant information needed to document the medical care of the patient.

Adaptive medical information intake may also involve adapting to a user type or role by providing specific information related to specific roles of users accessing a clinical documentation system. For example, a nurse may be presented with different information than a physician. Physicians, nurses, and patients may be associated with different types of form sections and templates, containing specialized information relating to the role of the user.

A clinical documentation system may be configured to react to user input with suggestions that are sensitive to context specific to the patient. For example, causes of shortness of breath in an elderly patient may be provided based on information identified from an EMR for the patient. The context involved would indicate that causes of shortness of breath in a child would not apply because of an age identified for the patient. Similarly, an elderly patient presenting a problem of back pain may cause a clinical documentation system to prompt a user to ask four selected questions relevant to elderly patients amongst a total of 16-20 risk assessment questions relating to back pain for all possible types of patients.

A clinical documentation system may rely on prior clinical knowledge to support context sensitive suggestions for integrations of sections into a form. The different sources of prior knowledge may include ontologies to describe arbitrary contexts, clinical information and practice settings, clinical guidelines and workflows, prior patient EMRs, or any other source of clinical knowledge that may be useful in determining inferences for form assembly and creation. The use of both general and site-specific prior knowledge and information in a clinical documentation system increases the ability of the system to adapt and customize functionality for different users and different medical facilities.

Further, a medical documentation system may involve knowledge content management so as to allow for efficient use of resources. Some knowledge or information bases and/or application functions may be better suited or specifically designed for certain situations. Therefore, adaptive clinical documentation systems may provide for adaptive use of knowledge bases and application functions to further tailor the adaptive nature of the system to specific context driven situations as well as specific patients. Thus, as the context of an implementation of a system changes, the informational content of the system may change adaptively to suit the changes. Further, content that is not required, or specifically tailored, to the changes may be unloaded to free resources for further use by the system.

In an embodiment two combined graphical models may be used in a clinical documentation system. The first graphical model may infer new sections to be added to a medical form document given a set of medical terms determined from an EMR of a patient. Another graphical model may infer new relevant medical terms or concepts associated with sections for a form of a clinical documentation system. The two models may also be modeled as a singular unified graphical model.

In an embodiment, a document model, a mapping model, and a domain model may be used. The document model outlines the structure a document may take. For example, multiple forms, form sections, subsections, elements, or questions may have rules associated with their respective presentation, content, and structure, and a document model may contain and enforce those rules. The domain model may be operable to link terms or concepts with other terms and concepts. The mapping model may be operable to link particular terms and concepts with the document model. For example, a weighted probabilistic network model may indicate links between specific terms and document elements such as form sections. The whole of the weighted probabilistic model may contain all possible connections between terms and form sections. When data is input into the three model system, inferences may be made using the three model system such that iterative analysis of input data may present acceptable levels of probability that proper form sections are included. For example, data including an age and gender may be input. Some connections in probabilistic network may be reduced to zero probability, or dropped, based on the data. In this example, the entry of Male may reduce the probability the patient is pregnant to 0%, and thus no sections relating to pregnancy will be included in a final document or form. As indicated above, as more data is input into the system, the process may work iteratively based on the additional data. In this example, the patient may be requested for an age, and provide information indicating that the patient is 10 years old, which in turn may reduce other probabilities in the model such as the probability the patient has Alzheimer's disease. The combined data may also be used to cumulatively reduce probabilities. In this example, the information indicating the patient is male may reduce the probability of the patient have breast cancer to 20%, and the information indicating the patient is 10 years old may further reduce the probability connection of the patient to breast cancer to 2%. Also, the domain model may analyze the input information to find associated information to provide the probabilistic network model to further update the probability connections. The iterative nature of providing and requesting information may continue until all probabilities are found acceptable, or found to be stable such that the entry of further information may not significantly affect the probabilities of the model. When a model reaches a steady probability state, a final document having form sections related to the remaining probable connections may be produced based on the rules of the document model. In an embodiment, the process may be continually iterative, and update probabilities and/or request further information continually as new information is input.

In an embodiment, a domain model may involve multiple knowledge bases. Individual knowledge bases may be selected as needed to make up the domain model for particular context driven situations. For example, the context of a situation may involve a woman being treated by a registered nurse in an emergency room. In this type of specific context situation, individual knowledge bases related to situational elements such as female patients, registered nurses, and emergency room practice may be selected for use with the domain model. Further, specific applications may be used to interact with the individual knowledge bases in the domain model. For example, a knowledge base for female patients may be operational in many practice settings, but an application specifically configured for emergency room practice may be selected to interact with a knowledge base for female patients to allow for a specific application based on the above indicated context. In this way, multiple applications and knowledge bases by be selected and applied based on situational context for domain model deployment.

In an embodiment, a clinical documentation system may start with an initial user, which may be a medical practitioner or a patient, inputting data into a record. The data may be related to a presenting problem of a patient. The data may be as simple as a gender, age, or chief complaint. A set of relevant medical terms or concepts may be extracted from a record or group of records and fed as evidence to a first graphical model. The first graphical model may then output the most probable sections that may be included in a final form document given the set of relevant medical terms. Once information is provided for the most probable sections, a set of new relevant medical terms or concepts may be inferred by the second graphical model. The new set of relevant medical terms may be included with the initial set of relevant terms for use by the first model. Form sections may be generated all at once, or as determined applicable in real-time. If the document contains adequate sections based on predefined criteria, a final form document is produced. Also, in an embodiment, the document may be continually updated with new sections as new probable sections are identified based on input data.

FIG. 1 shows a flow chart diagram of an embodiment of a method for adaptive medical data collection. The method is implemented by a computerized physician order entry (CPOE) system, an automated workflow system, a review station, a workstation, a computer, a picture archiving and communication system (PACS) station, a server, combinations thereof, or other system in a medical facility. For example, the system or computer readable media shown in FIG. 3 implements the method, but other systems may be used.

Additional, different, or fewer acts may be performed. For example, an act for optimizing performance of a task of a workflow is provided. The method is implemented in the order shown or a different order. For example, acts 102, 104, 106, and 108 may be performed in parallel or repeated.

In act 102, an analysis of electronic records is triggered in response to information input into an EMR of a patient. The information may be input into electronic format through any method. In an embodiment, the information may be input into an electronic form of an EMR for a patient. In another embodiment, the information may be freely input into a generic EMR. For example, a user may speak into a microphone indicating a symptom. The patient may input the language "I have a headache" into the microphone where it is electronically transcribed to indicate a symptom. Any automated speech recognition method, such as Hidden Markov Models, Dynamic Time Warping, or Neural Networks, may be used.

The analysis may be triggered by any act. In an embodiment, the analysis is triggered based on recognition of an input of data into an EMR. Recognition of an updated field in an electronic form or database of an EMR of a patient may also trigger the analysis. The analysis may be performed using the information input into the EMR that triggered the analysis.

The electronic records may be any electronic record from which a potential diagnosis or treatment for a patient may be inferred independently, or in combination with other electronic records. For example, electronic records may include ontologies of arbitrary contexts, clinical data records, practice data records, clinical guidelines, EMRs of prior patients of a medical entity.

In act 104, a potential condition for the patient is determined based on the analysis. The analysis may be any analysis of electronic records capable of determining a potential condition for a patient. In an embodiment, the analysis involves the application of a machine learned model to the electronic records. For example, a Bayesian Network model trained using a Markov Chain Monte Carlo (MCMC) method may be used. In another example, an Expectation Maximization method based model may be used. The machine learned model may be trained using knowledge of an expert, or documented prior knowledge such as ontologies or medical databases. The model relates possible inputs as a feature vector for a patient to conditions.

A condition may involve any condition for a patient. In an embodiment, a determined condition involves a medical condition of the patient. For example, a condition may be heart disease, diabetes, epilepsy, hepatitis B, an allergy, or any condition related to the health or status of a patient. The condition is a possible diagnosis. A given input feature vector may indicate only one or more than one possible diagnoses and corresponding conditions.

In an embodiment, a probability that a patient has a condition is determined. The determined probability may be compared to a probability threshold, and if the probability meets a threshold it is determined that the condition applies to a patient. For example, a probability threshold may be 75% probability that a condition applies to a patient. Any determined probability larger than 75% may indicate that the condition applies to a patient. Any probability scoring system may be used. The machine learnt model may be probabilistic, so outputs a probability associated with one or more conditions.

In an embodiment, a probabilistic network may be used to determine possible conditions for a patient. The probabilistic network may have connections between terms or concepts and associated conditions represented by probabilities indicating that a current patient may have a condition. The probabilities may represent a current state of knowledge or data for a patient, and may be updated with inputs of additional information.

Multiple conditions may be determined to apply to a patient. A given model may provide more than one condition. Alternatively, different models, such as models specific to one or more conditions are applied to the data for the patient. Different models test for different conditions.

In act 106, additional information indicated as relevant to the potential condition of the patient is identified. The additional information may be associated with a condition determined for a patient, and identified upon determining that a condition applies to a patient. The additional information may involve any information relevant to determine a diagnosis for a patient. In an embodiment, the information may be determined to provide further indication that a condition applies to a patient. For example, if a patient indicates that they have a headache, other information such as history of headaches or recent physical injuries may be identified as relevant to a potential condition of persistent migraines, or post-concussion syndrome may be determined as potential conditions for a patient. All possible additional information may be stored in a collection, and relevant information may be identified from the collection. Additional information may be indicated as relevant through the application of a model, such as a machine learned graphical probabilistic model, as described herein.

Information may be configured as individual fields in a database associated with conditions, or collections of fields associated with conditions. When a condition is determined, or a possible condition is identified, fields associated with the condition may be identified. For example, a possible condition may be indicated with a probability of 73%, and all fields associated with the condition may be identified. Contrarily, if a probability of a condition is below a certain probability, such as below 35%, the fields associated with the condition may not be selected.

In an embodiment, additional information may be grouped as related to various conditions. For example, fields for the additional information may be assembled or contained in preformatted form templates. The form templates may each be associated with at least one condition. Once a condition is indicated, an associated form template may be identified. Multiple form templates may also be identified.

In an embodiment, additional information may be identified as individual fields for the additional information, wherein the individual fields are associated with a condition. All fields determined to be associated with a condition above a certain probability may be identified.

In act 108, a request for the identified additional information is generated. The request may involve selecting an established collection of information associated with the determined potential condition of the patient.

In an embodiment, the established collection of information is a preformatted medical form or form section. The form is electronic and may be a collection of fields associated with an EMR of a patient. The fields may be used to record and store the information associated with a condition. The fields may be clear of data, and configured for inputting information into an EMR, or other database. In an embodiment, the fields may have standardized information contained in them relating to a condition. For example, the standardized information may indicate that a certain dosage of acetaminophen is a typical treatment for a patient with a headache condition.

In an embodiment, some of the fields may be pre-populated with information for the patient pulled or mined from other portions of the EMR. For example, an age of the patient may be determined from other areas or individual records of an EMR, and the age may be pre-populated in the form. In another embodiment, the fields having information mined from an EMR will be withheld from presentation with the form. The information, however, may still be noted and associated with the condition for the patient. For example, a form may not indicate an age for a patient, but an age is determined, and a dosage for a medication may be determined based on the condition and the mined age of the patient. Any data mining may be used, such as is disclosed in U.S. Pat. No. 7,617,078, the disclosure of which is incorporated herein by reference.

In an embodiment, a collection of form templates or sections may be stored, each associated with a particular condition and containing fields for information relating to the condition. Form templates relating to conditions determined for a patient may be selected and presented on a display as part of generating a request for identified information relating to the conditions. The form templates may be presented in a pre-formatted whole, containing fields for all identified information relating to a condition. The form templates may also be presented in part, displaying only fields relating to information identified as most critical to diagnosis or treatment of the condition.

Multiple form templates for different conditions may be displayed at once as a singular form, or separately. If different forms include requests for the same information, the forms may be merged to provide one request rather than duplicative entry.

In an embodiment, condition determination may be iterative. A portion of the identified additional information may be received. Other information regarding the potential condition of the patient may be identified based on the received identified additional information. The analysis may be re-performed using the other information to identify further information relevant to the potential condition of the patient, and a second request for the further information may be generated. Numerous inputs of information and requests may be generated during an iterative process of adaptive medical information input to determine a diagnosis or treatment of a condition.

In an embodiment involving machine learned models, the performing and re-performing an analysis may be undertaken by applying a first machine learned model and the identifying other information may involve the application of a second machine learned model. The second machine learned model may receive the identified additional information and generate the other information. The other information may be additional terms or medical characteristics that may be added to the analysis of the first machine learned model to provide higher accuracy for determining information, or forms, pertinent to the patient. As such, there may exist a form hierarchy wherein a general condition, such as head pain, has a general form template designed to gather further information to further diagnose and narrow the head pain condition. For example, the request for information may involve a query for information to determine if a patient has a concussion, or if the patient suffers from chronic migraines, each of which may have respective forms in the hierarchy, with fields for specific information relating to each condition. The second machine learned model may be designed to take the input from the initial request, and combine the information with other information to further output a potential diagnosis for a condition that may be input into the first model to identify further forms.

Figure 2:
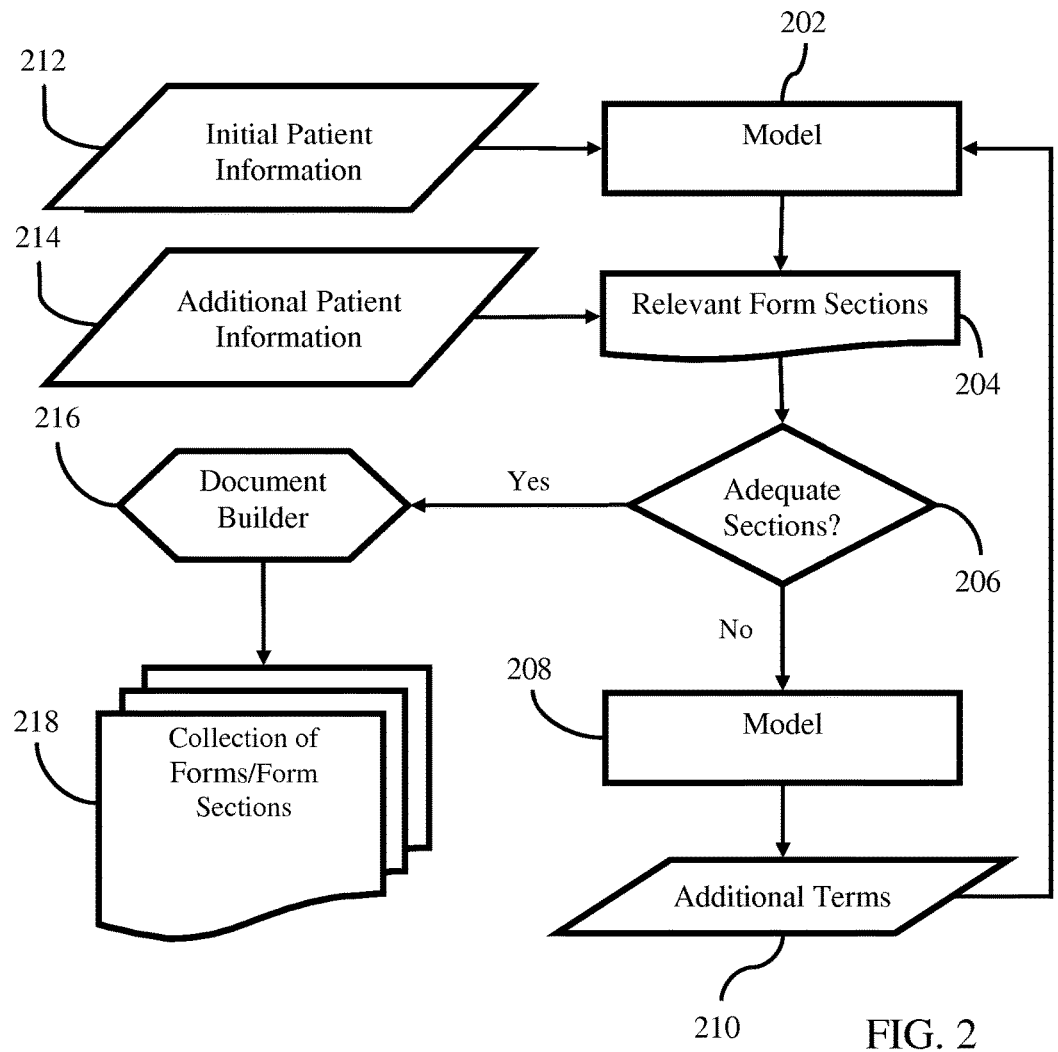
FIG. 2 is a flow chart diagram of another embodiment of a method for adaptive medical data collection.

FIG. 2 shows a flow chart diagram of an embodiment of adaptive medical data collection. The diagram may describe the operation of a system, such as that described with respect to FIG. 3 below, or another structure operably consistent with the diagramed components.

An analysis of electronic records using a model 202 may be triggered in response to information 212 input into an EMR of a patient. The model 202 may determine a potential condition for the patient based on the analysis. The model 202 may identify additional information contained in form sections 204 indicated as relevant to the potential condition of the patient. A request for the identified additional information may be generated by selecting a medical form or form section 204. The form or form section 204 may be determined relevant and selected based on a probability a patient has a condition associated with the form determined by the model 202. Form sections 204 may be entire forms, or sections of forms designated for certain conditions. The relevant form sections 204 may be displayed for data presentation or data input.

Adaptive medical data collection may be iterative. An iterative embodiment may involve receiving at least a portion of the identified information. For example, additional patient information 214 may be input into some, or all, of the fields of relevant form sections 204. Using a second model 208, other information or additional terms 210 may be identified or determined regarding a potential condition of a patient based on the received identified information. The analysis may be re-performed by a first model 202 using the additional terms 210 to identify further relevant form sections 204.

Iterations may continue until is determined in act 206 that there is enough, or adequate, requested or presented information, or whether there have been adequate form sections identified, generated, and/or presented. The determination may be made based on predefined criteria. In an embodiment, a minimum number of form sections may be required. In an embodiment, an adequate section determination 206 may be made based on probabilities of a condition for a patient. For example, form templates associated with conditions determined beyond a threshold may be provided. Further, conditions within a range of probabilities may require iterations to better establish a likelihood the patient has the condition. The model 208 may refine the information contained by providing additional terms to use with the model 202 to select further relevant form sections 204. For example, iterations may be provided for conditions determined with a probability of 45% to 75%, where 75% may be the probability threshold. Iterations may continue until all probabilities determined for all conditions are either below 45%, or above 75%.

In an embodiment, when it is determined that there are adequate form sections, a document builder 216 may be used to create a total collection of forms/form sections for generation or presentation. The document builder 216 may also be included in a non-iterative embodiment, after relevant form sections 204 have been determined by the model 202. The collection of form sections 218 may be presented in an order according to a set of ordering or ranking rules. In an embodiment, form sections may be ranked by probability of a patient having the condition associated with the form section, with the highest probabilities being placed most prominently in a collection of form sections 218. Examples of prominent placements of form sections 204 may include being placed at the top of a collection 218, displayed with highlighted or more noticeable text than other form sections of the collection 218, or a form section may require input prior to inputs of other sections.

In an embodiment, the models 202 and 208 may be one unified model. In an embodiment, the models may be machine learning models. The models 202 and 208 may be trained based on a collection of prior medical knowledge to represent and efficiently manipulate a probability distribution of conditions for a patient associated with document sections 206. Document sections 206 associated with a condition determined to a certain probability to apply to a patient may be included in a personalized main document 218. The main document 218 may group relevant subsections 206 that contain information needed to be registered for a given patient in a given clinical visit. The relevant subsections 206 included in a main document 218 are associated with conditions having a probability of relating to a patient. The probability of relating to a patient may be modeled using the machine learned model 202, which may be a generative probabilistic model such as a Bayesian Network model. The generative probabilistic model may represent relationships among medical concepts or terms and document sections such as term-term relations, sections-term relations, sections-terms relations, and section-section relations.

Probabilistic graphical models are graph-based representations for encoding a distribution over multi-dimensional space, wherein each node in a graph represents a random variable. Links between nodes specify a direction or relevance of an association. The edges of the graph each have an associated real number usually referred to as an exponential family weight. A positive link weight between two nodes means that an increase or decrease in the value of node 1 causes an increase or decrease, respectively, in a value for linked node 2. A negative link weight indicates a decrease value for node 1 increases the value for node 2 or vise versa. The absolute value of the weights is a measure of strength of influence by any parent node on a child, or linked, node. A node in a graphical model may encode either discrete or continuous probability distributions.

Graphical models for adaptive medical information input may be trained in two steps. The first step involves learning or designing the structure of the network. The first step may be performed by an expert in the knowledge of the medical area and form constructs being graphed, by a prior form knowledge structure, or automatically through a learning algorithm such as a Markov Chain Monte Carlo (MCMC) local search method. For example, an expert may recognize that a particular form may be associated with a particular condition. An expert may also recognize that the information in one form is related to information in another form. These associations may be recorded and integrated to form the structure of the network. The first step may also involve a hybrid creation which may consist of applying an automatic algorithm first and later modifying the resulting network using known relations, an expert, or prior knowledge.

A second step in training a graphical model for adaptive medical information input may involve learning the parameters of a network including unrealized relationships between conditions and forms, or strength of associations between forms and conditions. In an embodiment, an Expectation Maximization search algorithm may be used. Such an embodiment may alternate between solving two problems, an expectation and a maximization, to compute maximum likelihood estimates of parameters for the model. The algorithm may start with random initializations of model parameters, and converge onto optimal point estimates, resulting in a network of nodes relating to conditions and associated form sections.

Once a model is trained, a set of evidences may indicate a probability that a given section should be included in a current personalized collection of forms 218. The evidences may include information such as patient characteristics, complaints, or sections already included in a document. Probabilities may be determined by a model using any method. In an embodiment, a Junction Tree algorithm is used.

Figure 5:
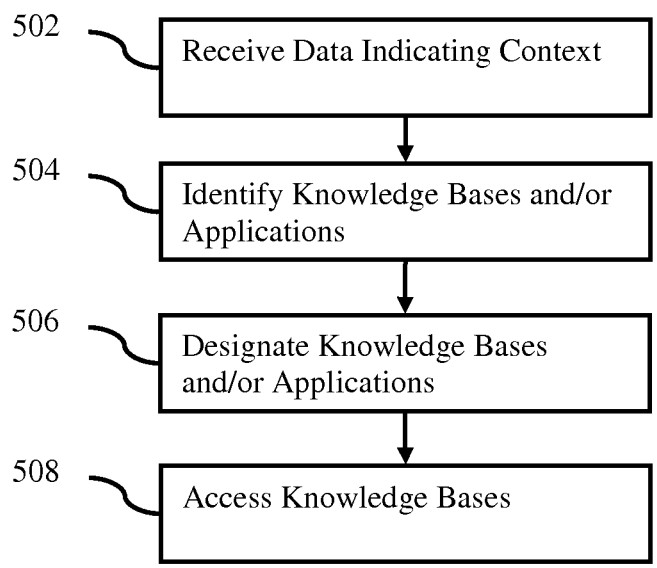
FIG. 5 shows a flow chart diagram of an embodiment of a method for adaptive medical data collection using content management.

FIG. 5 shows a flow chart diagram of an embodiment of a method for adaptive medical data collection using content management. The method is implemented by a computerized physician order entry (CPOE) system, an automated workflow system, a review station, a workstation, a computer, a picture archiving and communication system (PACS) station, a server, combinations thereof, or other system in a medical facility. For example, the system or computer readable media shown in FIG. 3 implements the method, but other systems may be used.

Additional, different, or fewer acts may be performed. For example, an act for optimizing performance of a task of a workflow is provided. The method is implemented in the order shown or a different order. For example, acts 502, 504, 506, and 508 may be performed in parallel or repeated. Also, the method may involve more or fewer acts. For example, an embodiment may involve only acts 502, 504, and 506.

In act 502, data indicating a context is received. The context may relate to a deployment of the method in a particular situation. As such, the situation may involve situational elements. Situational elements may involve a type of patient (i.e. a female or male patient), a type of practitioner (I.e. a nurse or surgen), a location of the deployment (i.e. operating room or emergency room), or any other element related to a clinical or diagnostic situation. In an embodiment, the situational elements may involve a medical identifier code of a workstation, a specialty of a physician (e.g., identity of a logged on user), a medical history of a patient, or a location of a medical room housing or hosting the clinical or diagnostic situation. Multiple situational elements may also be received. Also, context may be determined from situational elements independently or in combination.

Situational elements may be received in any format or combination of formats. In an embodiment, data indicating a situational element may be manually entered. For example, a user may manually enter a user identification code such as a user ID. This user ID may indicate situational elements. In another embodiment, a user may select from specific options for situational elements related to the context of the situation, such as selecting the emergency room from a menu. In another embodiment, a patient identifier may be entered and situational elements may be mined from stored patient information such as in an EMR of a patient. For example, the patient ID may indicate that the patient has a diabetes condition. A diabetes situational element may then be received.

Situational elements may be entered into an application in operation remote to the system performing the method as described herein. For example, information may be entered into an application on a workstation deployed in an emergency room, whereas the method may be performed in separate locations from the emergency room, such as in a computer operations server location located remotely from the emergency room. In another example, situational elements may be entered into an internet browser and communicated through one or more networks to reach the actual location of reception of data representing situational elements. In an embodiment, the situational element may be related to the location and/or the identity of a user located remotely from a system or device performing the method. A remote location may be a location involving physical separation or removal from a system performing the method. For example, a remote location may involve a different room of the same facility, a different facility, or a different town or city.

In act 504, a knowledge base and/or an application associated with the indicated context or situational elements may be identified. Further, multiple knowledge bases and/or applications may be identified based on the received data indicating a context. In an embodiment, at least one application from a plurality of applications, and at least one knowledge base from a plurality of knowledge bases associated with the received situational elements, are identified. Knowledge bases and applications may be identified using the same or different situational elements for a given context.

An application may be any type of application. For example an application may be an Application Programming Interface (API) that specifies or controls the interaction between software on a system. In an embodiment, APIs may be associated with knowledge bases. For example, a female patient knowledge base may be interacted with using a nurse API that provides a specific way of interfacing with the female patient knowledge base designed for a nurse.

A knowledge base may be any type or collection of data. For example, a knowledge base may be a full relational database or a single dimensioned table or array. The knowledge base represents information associated with a specific situation, such as information for nurses or female patients. The knowledge base may be information alone or may include relations or functions for the situation. In an embodiment, a larger knowledge base may involve a collection of smaller knowledge bases. For example, a cardiology knowledge base may involve a collection of multiple knowledge bases such as a heart failure knowledge base and/or a cardiomyopathy knowledge base. In such an embodiment, the smaller knowledge bases may be considered a singular knowledge base, or a part of the larger knowledge base.

Also, applications and/or knowledge bases may have an associated hierarchy. The hierarchy may indicate that certain applications and/or knowledge bases may operate on or within other applications and/or knowledge bases. For example, an emergency room application may have sub-applications which are particular to user specialties such as ER nurse or ER physician to provide a specialized environment for the user. In such a case, a context that indicates the sub-application will implicate the application located higher in the hierarchy, in this case the emergency room application.

In an embodiment, context may be derived from situational elements, and an ontology model may be used to associate knowledge bases and/or applications with contexts.

In an embodiment, multiple versions of particular knowledge bases, applications, or services may be used. Different versions of each may be associated with different situational elements or indicated contexts.

In act 506, identified knowledge bases may be designated as active. Identified applications may additionally or independently be designated as active. Also, knowledge bases or applications not identified as associated with the indicated context or situational elements may be designated as not active or inactive. An active designation may provide an indication to a system implementing the method to use system resources to load or otherwise activate knowledge bases and/or applications designated as active. In an embodiment, an active designation may also manipulate a knowledge base such that an active knowledge base may be accessed to provide data for document creation.

In an embodiment, knowledge bases or applications may have been designated as active previous to the reception of situational elements. These previously designated active knowledge bases or applications may be designated as not active, or similarly have the active designation removed, if the knowledge bases or applications are not associated with the indicated context or situational elements.

Also, knowledge bases or applications may be designated as active in response to the reception of situational elements, but may only be used to initialize or provide background info for other knowledge bases or applications. These knowledge bases or applications may then have the active designation removed. These types of uses may be indicated in characteristics associated with specific knowledge bases or applications, and specific knowledge bases or applications may designate other knowledge bases or applications that are required to be activated prior to their use.

Knowledge bases or applications may also be designated as not active if the knowledge bases or applications are associated with the indicated context or situational elements, but conflict with other active knowledge bases or applications. In an embodiment, knowledge bases and/or applications include characteristics, and these characteristics may be compared to determine conflicts. For example, a knowledge base that has characteristics that indicate that the knowledge base may only be used with nurses may not be designated as active along with a knowledge base that is designated for use only with physicians, as these user roles may be designated as distinct and incompatible. In another example, a first and a second knowledge base may both have "female" characteristics associated. In such a situation, one of the conflicting knowledge bases may be designated as active, and the other designated as inactive.

In an embodiment, a knowledge base of two knowledge bases having a more recent update date or revision level may be designated as active, and the other as inactive. Redundancy of knowledge bases may also be determined in this way. For example, there may be particular categories of knowledge bases where only one knowledge base may be designated active at a given instance. For example, a "Gender" category may only allow a singular knowledge base to be designated as active depending on received patient context.

In an embodiment, characteristics do not have to match explicitly to determine conflicts or redundancy. Characteristics for knowledge bases may include some like contexts and other different contexts. For example, context elements may indicate that a female patient is being treated in an emergency room, and one knowledge base may have a "female" characteristic, while a second knowledge base may have a "female" characteristic as well as an "emergency room" characteristic. In such a case, the knowledge base having more specific characteristics applicable to the context may be chosen, in this case the second knowledge base.

In act 508, knowledge bases designated as active are accessed. Knowledge bases may be accessed using applications that have been designated as active. Active knowledge bases may be accessed to provide information for generating a document based on situational elements of a context. In an embodiment, a clinical context involving situational elements such as a female patient being attended by a nurse in an emergency room may indicate that a specific knowledge base for female patients be accessed using an application designated for use by a nurse in an emergency room.

Where multiple knowledge bases and/or applications have been selected for a specific context, the knowledge and/or applications may be combined. For example, the same information in different knowledge bases or applications is identified and repetition is avoided. As another example, differences are identified and requests, presentation, guidance, or other characteristics of documentation for the differences are processed sequentially or in parallel.

Accessed information may be used to provide specific documentation for a specific clinical situation, for example as described above with respect to FIG. 1 and FIG. 2.

Figure 6:
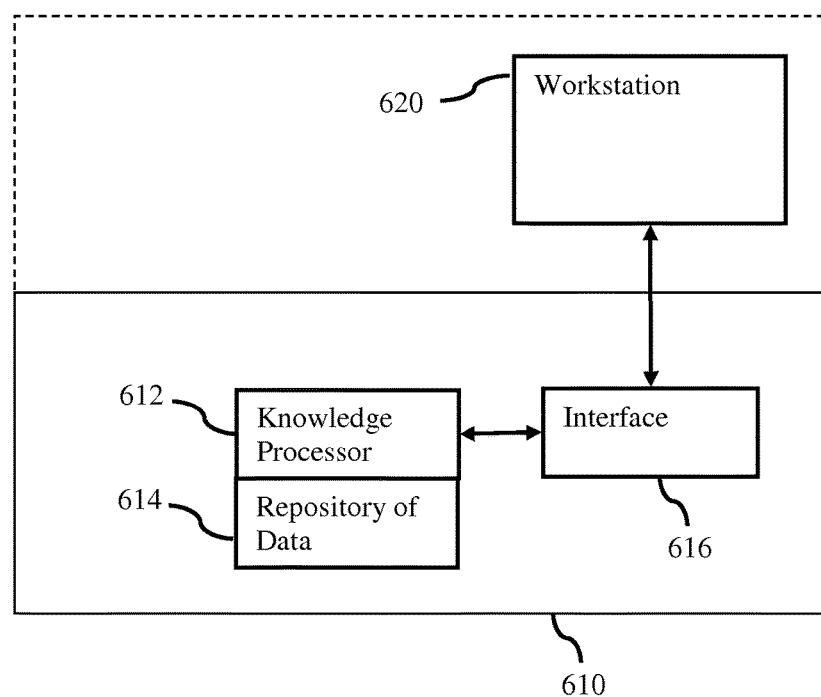
FIG. 6 illustrates a system for generating a document from a selection of application functions and knowledge bases.

In FIG. 6, a system 610 for generating a document from a selection of application functions and knowledge bases is illustrated. The system 610 involves a knowledge processor 612 that communicates with a repository of data 614 and an interface 616. The interface 616 may communicate with a workstation 620. In an embodiment, the workstation 620 may be an integrated component of the system 610. In another embodiment, the workstation 620 may be an external or remote system in communication with the system 610. Further, an embodiment may provide that the workstation 620 is physically removed from the system 610, but considered a part of the system 610, such as may be illustrated by a client-server arrangement where the workstation 620 is the client and the system 610 is the server. Each of the illustrated components may be implemented using a system as described with respect to FIG. 3. Further, the components may be implemented using distinct or shared hardware. For example, the knowledge processor 612 and the repository of data 614 may be implemented using the same processor, multiple shared processors, or different processors. Also, in an embodiment where the workstation 620 is a component of the system 610, the knowledge processor 612 and the workstation 620 may be implemented using same processor, multiple shared processors, or different processors.

The workstation 620 may be deployed in a context laden environment driving content selection for the system 610. For example, the workstation 620 may be deployed in a location such as an emergency room and thus may indicate or otherwise provide an emergency room related situational element to the system 610. Further, the environment specific to a user at the workstation 620 and the operations of the user with the workstation 620 may indicate situational elements such as a user role, patient role, or patient characteristics. The situational elements may be manually entered at the workstation 620, or automatically determined. In an embodiment, the workstation may include a network location or other location determining functionality that may indicate a location of the workstation. Other situational elements may also be automatically determined. For example, a patient may be identified at the workstation 620 and medical records may be accessed for the patient, or other patients, to determine medical conditions or characteristics of the patient. Automatic determination of situational elements may be performed at the workstation 620, within the system 610, or using any other system functional to return the situational elements.

In an embodiment, the repository of data 614 involves a plurality of executable application functions and a plurality of associated knowledge bases. The interface 616 receives data specifying situational elements indicating a context from an application remote to the plurality of application functions. For example, the application may be a software application operating on the workstation 620 which is implemented in a particular location by a particular user who is diagnosing a particular patient that has particular patient characteristics. The knowledge processor 612 may determine at least one executable application function associated with the indicated context or directly with the received situational elements. The knowledge processor 612 may also, or in the alternative, determine at least one knowledge base associated with the indicated context or directly with the received situational elements. The knowledge processor 612 may designate as active at least one knowledge base associated with the determined application function and/or the indicated context. The knowledge processor 612 may designate as inactive at least one knowledge base not associated with the determined function or the indicated context. The knowledge processor 612 may then provide data from at least one active knowledge base to the remote application. The provided data may be operational to generate a document based on at least the provided data, for example as described above with respect to FIG. 1 and FIG. 2.

A repository of data may be considered a container or collection of knowledge bases and/or applications, as well as associations between the knowledge bases and/or applications with specific situational elements, or combinations of situational elements which may be considered a scenario. Further, a designation of active for a knowledge base or application may indicate to the system 610 generally, or the repository of data 614 specifically, that the knowledge bases and/or applications designated as active will be loaded onto an active memory or otherwise acted upon by the system 610 to make them accessible by the system 610. Similarly, knowledge bases or applications not marked as active may be removed from system 610 resource consideration. These not active knowledge bases or applications may be removed from an active memory immediately or may be deleted as space and resources are required by the system 610.

Knowledge bases and/or applications may be associated with situational elements, or context indicated by the situational elements, using any technique. In an embodiment, the system 610 may evaluate context indicated by the situational elements against an ontology model that describes knowledge bases. For example, a context indicated by situational elements may also be considered an operational scenario that may be determined from the situational elements using an ontology model to group and identify terminology from the situational elements. Further, specific combinations of knowledge bases and/or applications may be associated with scenarios. In an embodiment, the combination of knowledge bases and application functions may be considered a service that may be provided by the system 610. Further, multiple scenarios may be associated with particular knowledge bases and/or applications, as well as knowledge base and/or application combinations.

In an embodiment, a context may be derived using a categorized structure for situational elements. The categorized structure may involve a determined category for each situational element received. For example, a context may involve a workstation 620 deployed in an emergency room. In such a context, a "Location" category may be determined as "Emergency Room." Similarly, other categories may be determined for other received situational elements. The combinations of determined categories may indicate a scenario which may be associated with a particular service. For example the situational elements may include "Female" and "Emergency Room." The scenario may involve a specific combination of a "Female" knowledge base and an "Emergency Room" application to operate with the "Female" knowledge base. This combination of knowledge base and application may be a "Female Emergency Room" service. A scenario may involve any combination of situational element categories, or be defined by such categories. Scenarios may involve, but are not limited to, Gender, Location, Specialty, Medical Condition of Patient, Medical Role of User, and/or Medical Specialty of User.

In an embodiment, categories may have required knowledge bases and/or applications that must be indicated as active when a situational element is received that indicates a value for the category. For example, a "Location" category may have specific applications that must be run in specific locations such as an emergency room. These required knowledge bases and/or applications will be designated as active and will be given precedence during conflict analysis.

Received situational elements do not need to explicitly match specific terms associated with services, individual knowledge bases, or applications. As indicated above, an ontology may be used to associate situational element terms with similar subjects to determine specific service associations with specific situational elements scenarios. For example, a situational element may indicate that a "Female" is in an "Urgent Care" location. An ontology may group "Urgent Care" with an emergency care subject that may be associated with an "Emergency Room" application.

In an embodiment, situational elements may also be associated with multiple applications and/or knowledge bases. For example, a situational element may be a name of a user, such as "Mary Joice." An associative table in the system 610 may indicate that Mary Joice is an OB-GYN physician. Consequently there may be a general "Physician" knowledge base associated with all physicians, and a physician specialty knowledge base of "OB-GYN" that may also be associated. In such an example, the "Physician" knowledge base and the "OB-GYN" specialty knowledge base may be operationally compatible such that the specialty "OB-GYN" knowledge base may provide more details related specifically to the specialty and function in parallel or otherwise support the general knowledge base. In another embodiment, characteristics of the multiple associated applications or knowledge bases may indicate that there are conflicts or redundancies that may be resolved as indicated above.

Figure 3:
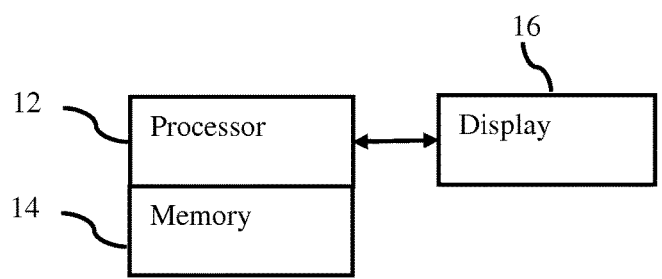
FIG. 3 is a block diagram of one embodiment of a system for adaptive medical data collection.

FIG. 3 shows a system for adaptive medical data collection and/or presentation. The system is a server, network, workstation, computer, database, or combinations thereof. The system 10 includes a processor 12, a memory 14, and a display 16. Additional, different, or fewer components may be provided. For example, the system includes a scanner, a network connection, a wireless transceiver or other device for receiving patient information and/or communicating patient information to other systems.

The memory 14 is a buffer, cache, RAM, removable media, hard drive, magnetic, optical, database, or other now known or later developed memory. The memory 14 is a single device or group of two or more devices. The memory 14 is shown within the system, but may be outside or remote from other components of the system, such as a database or PACS memory.

The memory 14 stores EMRs for patients and other medical data relating to conditions of patients of a medical facility. Models, such as probabilistic graphical models trained using medical data may also be stored on the memory 14. Multiple EMRs of other patients may also be stored on the memory 14. In an embodiment, the memory 14 is operable to store a plurality of electronic medical records of a plurality of patients of a medical entity, specific electronic medical record of a patient as well as ontologies, electronic clinical information, practice settings, machine logs, clinical guidelines, and workflows. The memory may also be operable to store a collection of knowledge bases and/or applications intended to operate using the knowledge bases.

The memory 14 is additionally or alternatively a non-transitory computer readable storage medium with processing instructions. The memory 14 stores data representing instructions executable by the programmed processor 12 for adaptive medical information input. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

In an embodiment, the instructions may include triggering a probabilistic network analysis of electronic records in response to information input into an Electronic Medical Record (EMR) of a patient, determining a potential condition for the patient based on the probabilistic analysis, identifying additional information indicated as relevant to the potential condition of the patient, generating a request for the identified additional information, receiving at least a portion of the identified additional information, and re-performing the probabilistic network analysis of electronic records using the received at least a portion of the identified additional information to update at least one probability of the probabilistic network.

In an embodiment, the instructions may include receiving data comprising situational elements, identifying at least one application from a plurality of applications, and/or at least one knowledge base from a plurality of knowledge bases associated with the received situational elements, and designating the identified at least one knowledge base as active.

The processor 12 is a server, general processor, digital signal processor, graphics processing unit, application specific integrated circuit, field programmable gate array, digital circuit, analog circuit, combinations thereof, or other now known or later developed device for medical category determination. The processor 12 is a single device, a plurality of devices, or a network. For more than one device, parallel or sequential division of processing may be used. Different devices making up the processor 12 may perform different functions, such as a handwriting detector by one device and a separate device for communicating or processing the detected handwritten data. In one embodiment, the processor 12 is a control processor or other processor of a computerized data entry system for an EMR storage or database system. The processor 12 operates pursuant to stored instructions to perform various acts described herein.

The processor 12 is configured by software or hardware adaptive medical information input. The processor 12 may be configured to trigger an analysis of electronic records stored on the memory 14 in response to information input into an EMR of a patient. The processor 12 may further be configured to identify additional information indicated as relevant to the potential condition of the patient from the other medical data. The processor 12 may also be configured to generate a request for the identified additional information. The request may be presented on the display 16. A collection of requests may also be presented on the display 16.

In an embodiment, the processor 12 may be configured to receive data comprising at least one situational element. The processor 12 may also be configured to identify at least one knowledge base from a plurality of knowledge bases using the at least one situational element. The processor 12 may be further configured to designate at least one identified knowledge base as active, and designate at least one knowledge base as inactive that was not identified using the at least one situational element.

The display 16 is a CRT, LCD, plasma, projector, printer, or other output device for showing an image. The display 16 displays a user interface with an image. The user interface may be for the entry of information, such as information that may be used for triggering an analysis of electronic records stored on the memory 14. The user interface may be for entering information into an EMR, or displaying a graphical model.

Figure 4:
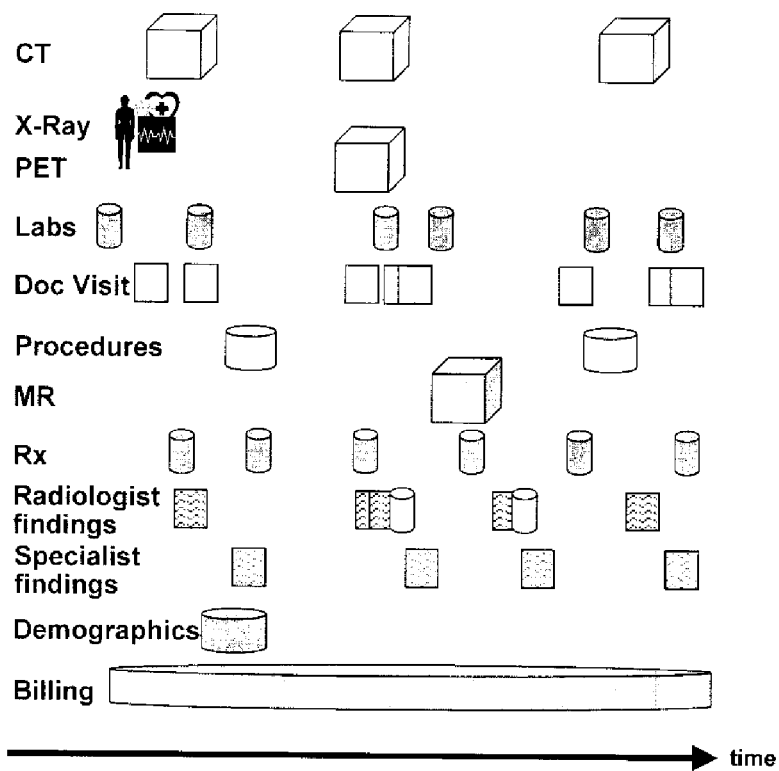
FIG. 4 is a representation of an electronic medical record.

FIG. 4 shows an exemplary EMR 200. Health care providers may employ automated techniques for information storage and retrieval. The use of an EMR to maintain patient information is one such example. As shown in FIG. 4, an exemplary EMR 200 includes information collected over the course of a patient's treatment or use of an institution. The information may be collected using forms, form templates, form sections, or combinations thereof. The information may include, for example, computed tomography (CT) images, X-ray images, laboratory test results, doctor progress notes, details about medical procedures, prescription drug information, radiological reports, other specialist reports, demographic information, family history, patient information, and billing(financial) information. Any of this information may provide for information related to a potential condition for a patient.

An EMR may include a plurality of data sources, each of which typically reflects a different aspect of a patient's care. Alternatively, the EMR is integrated into one data source. Structured data sources, such as financial, laboratory, and pharmacy databases, generally maintain patient information in database tables. Information may also be stored in unstructured data sources, such as, for example, free text, images, and waveforms. Often, characteristics, such as key clinical findings, are stored within unstructured physician reports, annotations on images or other unstructured data source.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for generating a document using at least one knowledge base, the system comprising:
a repository of data comprising a plurality of knowledge bases, each knowledge base being associated with a different situational element, wherein the situational element is one of a medical condition identifier code, specialty of a physician, medical history of a patient, and location of a medical room;
a computer readable active memory storing one or more knowledge bases designated as active;

an interface for receiving data comprising situational elements related to the clinical situation from an application remote to the repository of data; and a knowledge processor configured to:
in response to determining that new information is entered into an electronic medical record associated with a patient, apply a Bayesian Network model trained by a Markov Chain Monte Carlo method to the electronic medical record to determine a first situational element, determine a first at least one knowledge base associated with the first situational element, designate as active the first at least one knowledge base associated with the first situational element, determine a second at least one knowledge base associated with a second situational element, designate as active the second at least one knowledge base associated with the second situational element, identify, in the computer readable active memory, a third at least one knowledge base not associated with any situational element;

designate the third at least one knowledge base as inactive;

in response to designating the third at least one knowledge base as inactive, remove the third at least one knowledge base from the computer readable active memory; and provide data from the first and the second at least one active knowledge base to the remote application, the provided data operational to generate a document based on at least the provided data.

2. The system of claim 1, wherein the repository comprises an ontology model that associates knowledge bases and their applicable contexts.

3. The system of claim 1, wherein:
the repository further comprises a plurality of executable application functions, and
the knowledge processor is further configured to determine at least one executable application function associated with the indicated context.

4. The system of claim 3, wherein:
the repository associates an individual type of executable application function with a plurality of different operational scenarios, and
the knowledge processor is configured to use the indicated context to identify a relevant operational scenario and an application function associated with the operational scenario.

5. The system of claim 3, wherein
each knowledge base of the plurality of knowledge bases comprises a version indicator, and the repository associates individual types of executable application functions with an information base using the version indicator.

6. The system of claim 3, wherein
the repository associates individual types of executable application function versions with corresponding information bases.

7. The system of claim 1, wherein
the repository associates characteristics with individual knowledge bases; and the knowledge processor is configured to determine a conflict between the first and the second at least one active knowledge bases, and designate at least one of the conflicting knowledge bases as inactive based on the conflict.

8. The system of claim 1, wherein the repository associates characteristics with individual knowledge bases; and the knowledge processor is further configured to determine that the first at least one knowledge base of a plurality of different knowledge bases designated as active is redundant based on the characteristics, and designate the first at least one of the redundant knowledge bases as inactive based on the redundancy.

9. A method for generating a document at a workstation, the method comprising:
in response to determining that new information is entered into an electronic medical record associated with a patient, applying a Bayesian Network model trained by a Markov Chain Monte Carlo method to the electronic medical record to determine situational elements, wherein each situational element is one of a medical condition identifier code, specialty of a physician, medical history of a patient, and location of a medical room;

identifying, by a processor, at least one application from a plurality of applications and at least one knowledge base from a plurality of knowledge bases associated with the situational elements;

designating the identified at least one knowledge base associated with the situational elements as active;

designating as inactive at least one knowledge base (i) not associated with any of the situational elements and (ii) incompatible with at least one of the situational elements;

in response to designating the at least one knowledge base as inactive, removing the at least one knowledge base identified as inactive from a computer readable memory storing active knowledge bases; and accessing, by the identified at least one application, the at least one knowledge base designated as active to provide information to the workstation for generating a document based on the situational elements, wherein the document is an adaptable form constructed of one or more templates specific to the patient situation for documentation of the patient situation.

10. The method of claim 9, further comprising:
removing an active designation from at least one knowledge base that is not associated with the identified situational elements.

11. The method of claim 9, wherein the knowledge base not associated with the identified situational elements was designated as active prior to the receiving.

12. The method of claim 9, wherein the situational elements are comprised of at least two situational elements.

13. The method of claim 9, wherein identifying at least one other application involves the use of an ontology model that associates knowledge bases with contexts derived from at least one situational element.

14. The method of claim 9, wherein the knowledge bases of the plurality of knowledge bases comprise characteristics, and wherein the method further comprising:
determining a conflict between at least two knowledge bases identified as active; and
removing the active designation of one of the conflicting knowledge bases.

15. The method of claim 14, wherein at least one of the at least two knowledge bases determined to conflict was designated as active prior to the receiving.

16. A system for generating a document, the system comprising:
a repository of data operable to store a plurality of knowledge bases;
a computer readable active memory storing plurality of knowledge bases designated as active; and at least one processor configured to cause the system to:
receive data comprising at least a role of a user, wherein the role of the user includes a clinical specialty of the user;
identify at least one knowledge base from the plurality of knowledge bases using the role of the user;
designate the identified at least one knowledge base as active such that the active knowledge base may be accessed to provide data for an adaptable document customized for the role of the user;
designate at least one knowledge base as inactive that has not been identified using the role of the user if the at least one knowledge base is incompatible with the role of user;
in response to designating the at least one knowledge base as inactive, remove the at least one knowledge base identified as inactive from the computer readable active memory;
in response to receiving entry of a patient identifier from the user, retrieving an electronic medical record and applying a Bayesian Network model trained by a Markov Chain Monte Carlo method to the electronic medical record to determine situational elements, wherein each situational element is one of a medical condition identifier code, specialty of a physician, medical history of a patient, and location of a medical room;
identify at least one knowledge base from a plurality of knowledge bases using the situational elements;
designate at least one knowledge base associated with the situational elements as active.

17. The system of claim 16, further comprising additional memory operable to store a plurality of applications, and the at least one processor is further configured to cause the system to select an application from the plurality of applications using the situational elements, and access the at least one knowledge base designated as active using the identified application.

18. The system of claim 16, wherein the processor is configured to receive data indicating at least two situational elements.

19. The system of claim 18, wherein the processor is further configured to identify at least one knowledge base using a combination of the at least two situational elements.

20. The system of 19, wherein the processor is further configured to give priority to knowledge bases identified using a combination of situational elements, and designate at least one knowledge base as active based on the priority.

21. The system of 19, wherein the identified at least one knowledge base would not be identified using any of the at least two situational elements independently.

22. The system of claim 16, wherein the at least one knowledge base is identified using an ontology model that associates knowledge bases with contexts derived from combinations of situational elements.

23. The system of claim 16, wherein the knowledge bases of the plurality of knowledge bases comprise characteristics, and wherein the at least one processor is further configured to:
determine a conflict between at least two knowledge bases identified as active; and
remove the active designation of one of the conflicting knowledge bases.

* * * * *